US010385330B2

(12) United States Patent
Servoli et al.

(10) Patent No.: US 10,385,330 B2
(45) Date of Patent: Aug. 20, 2019

(54) EXTRACTION OF CIRCULATING NUCLEIC ACIDS

(71) Applicant: Biocartis N.V., Mechelen (BE)

(72) Inventors: Eva Servoli, Lausanne (CH); Patrick Van Den Bogaard, Morges (CH)

(73) Assignee: Biocartis N.V., Mechelen (BE)

( * ) Notice: Subject to any disclaimer, the term of this patent is extended or adjusted under 35 U.S.C. 154(b) by 243 days.

(21) Appl. No.: 15/100,882

(22) PCT Filed: Dec. 2, 2014

(86) PCT No.: PCT/EP2014/076301
§ 371 (c)(1),
(2) Date: Jun. 1, 2016

(87) PCT Pub. No.: WO2015/082495
PCT Pub. Date: Jun. 11, 2015

(65) Prior Publication Data
US 2016/0298106 A1    Oct. 13, 2016

(30) Foreign Application Priority Data

Dec. 2, 2013    (EP) .................................. 13005603

(51) Int. Cl.
*C12Q 1/68*      (2018.01)
*C12N 15/10*    (2006.01)
(Continued)

(52) U.S. Cl.
CPC ......... *C12N 15/1006* (2013.01); *B01D 15/12* (2013.01); *B01D 15/125* (2013.01);
(Continued)

(58) Field of Classification Search
None
See application file for complete search history.

(56) References Cited

U.S. PATENT DOCUMENTS 7,264,927 B2 * 9/2007 Nargessi .................. C12N 1/08
                                                                435/6.12
2010/0285469 A1 * 11/2010 Su ...................... C12N 15/1013
                                                                435/6.13
(Continued)

FOREIGN PATENT DOCUMENTS

JP    2006-311803 A    11/2006
JP    2013-511269 A     4/2013
(Continued)

OTHER PUBLICATIONS

El-Hefnawy et al. (Clinical Chemistry, 2004, 50:3, p. 564-573) (Year: 2004).*

(Continued)

*Primary Examiner* — Stephanie K Mummert
(74) *Attorney, Agent, or Firm* — Andrus Intellectual Property Law, LLP

(57) ABSTRACT

The present invention relates to a method for extracting circulating nucleic acids from a biological fluid. The method comprising the successive steps of providing the biological fluid supposed to contain the circulating nucleic acids. Then the biological fluid is contacted with a lysis solution comprising at least a chaotropic agent, a binding solution comprising at least a PEG derivative designed for cooperating with at least part of the circulating nucleic acids, wherein the binding solution is free of ethanol and isopropanol, and a solid support capable of capturing at least part of the circulating nucleic acid. Finally, the solid support is separated from the lysis solution, from the binding solution and from the biological fluid.

20 Claims, 1 Drawing Sheet

(51) Int. Cl.
  *C12Q 1/6806* (2018.01)
  *B01D 15/38* (2006.01)
  *B01D 15/12* (2006.01)
  *B01D 15/42* (2006.01)
  *B01D 39/16* (2006.01)
  *B01D 39/18* (2006.01)
  *B01D 39/20* (2006.01)
  *C12P 19/34* (2006.01)

(52) U.S. Cl.
  CPC ....... *B01D 15/3885* (2013.01); *B01D 15/424* (2013.01); *B01D 39/16* (2013.01); *B01D 39/18* (2013.01); *B01D 39/2003* (2013.01); *C12N 15/1013* (2013.01); *C12N 15/1017* (2013.01); *C12P 19/34* (2013.01); *C12Q 1/6806* (2013.01)

(56) References Cited

U.S. PATENT DOCUMENTS

2011/0097782 A1  4/2011  Jiang et al.
2013/0085681 A1* 4/2013  Deciu .................. C12Q 1/6827
                                                              702/19

FOREIGN PATENT DOCUMENTS

| JP | 2013-516984 A | 5/2013 |
| JP | 2013-536679 A | 9/2013 |
| WO | 2003/040687 A2 | 5/2003 |
| WO | 2005/021748 A1 | 3/2005 |
| WO | 2007/140417 A2 | 12/2007 |

OTHER PUBLICATIONS

QIAamp circulating nucleic acid kit (Qiagen, 3rd edition, Oct. 2013, p. 1-56) (Year: 2013).*
International Search Report for PCT/EP2014/076301 dated Mar. 3, 2015.
Written Opinion of the International Searching Authority for PCT/EP2014/076301 dated Mar. 3, 2015.
International Preliminary Report on Patentability for PCT/EP2014/076301 dated Jun. 7, 2016.
Office Action for JP2016-535661 dated Sep. 25, 2018.

* cited by examiner

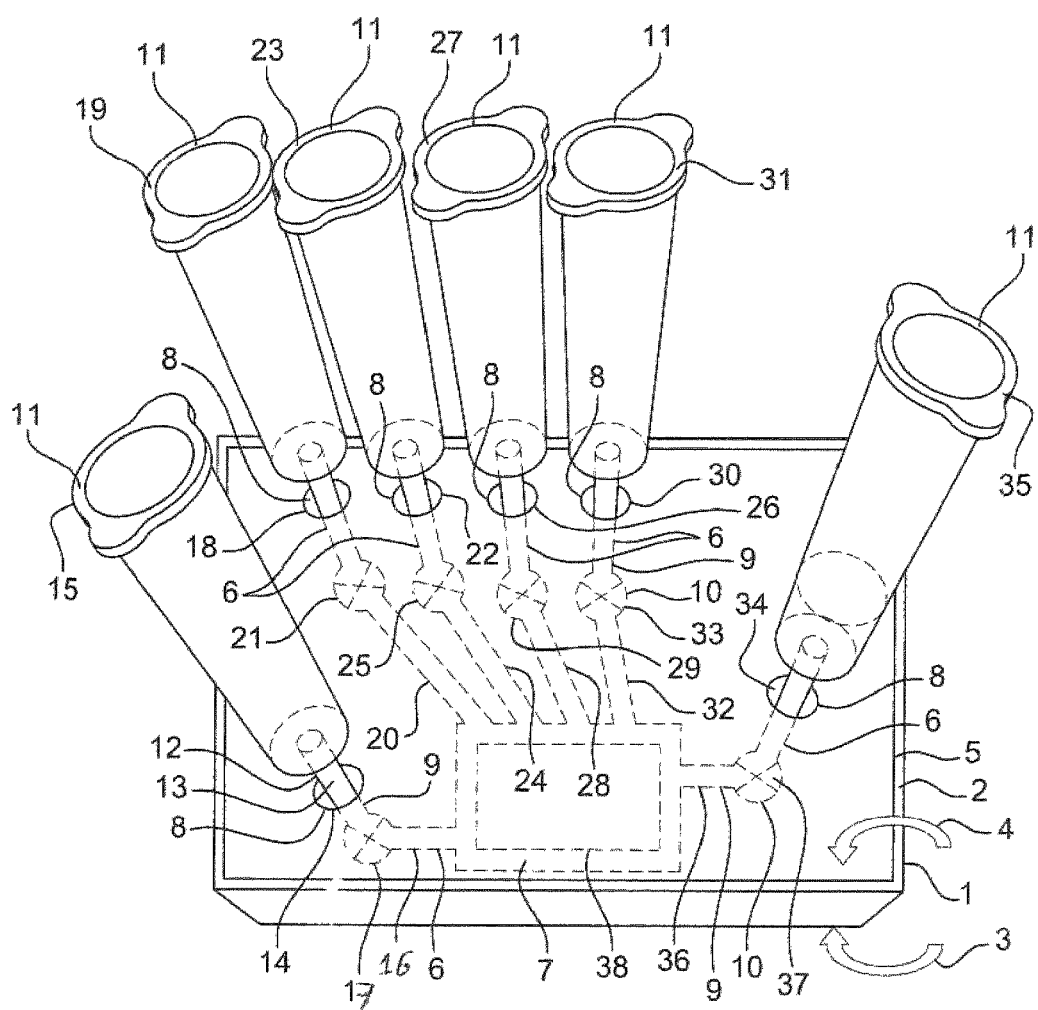

EXTRACTION OF CIRCULATING NUCLEIC ACIDS

CROSS REFERENCE TO RELATED APPLICATION

The present application is the U.S. national stage of International Application PCT/EP2014/076301, filed on Dec. 2, 2014, which international application was published on Jun. 11, 2015 as International Publication No. WO 2015/082495. The International Application claims priority to European Patent Application No. 13005603.9, filed on Dec. 2, 2013, the contents of which are incorporated herein by reference in their entireties.

The present invention relates to a method for extracting circulating nucleic acids from a biological fluid.

The introduction of non-invasive methods for accurate and early diagnosis of diseases such as cancer represents a promising solution to enhance the life expectancy of patients. In this respect, the analysis of circulating tumor nucleic acids comprised in a biological sample is a recognized diagnostic tool to either detect cancer in early stages or monitor the evolution of malignancies in the early stages of the disease. The concentration of circulating nucleic acids (ciNAs) in blood is reported to be five to ten times higher in patient suffering from certain cancers compared to healthy individual, however only a fraction of them may present a malignant mutation and therefore be diagnostically relevant.

ciNAs are known to be fragmented nucleic acids, comprising fragments of variable length with a majority of short fragments below three hundreds base pairs. Generally, the extraction protocols for extracting ciNAs are based on procedures which are initially designed for long fragments of nucleic acids such as genomic DNA (gDNA) and which are modified to further allow the extraction of the short fragments comprised in ciNAs. To that end, a binding enhancer solution, usually containing a guanidinium salts in an ethanol/isopropanol solvent mixture, is added to the biological sample.

Nowadays, the trend is to perform diagnostic assays on disposable cartridges made of polymeric materials. However, the assembly of the different parts that form such a cartridge requires the use of components, like adhesives, made of polymeric materials which are soluble in ethanol and/or isopropanol based solvents. Thus, the existing ciNAs extraction protocols using binding enhancer solutions are not compatible with disposable cartridges as delamination would rapidly occur, thereby causing problems when trying to conduct the extraction protocol on such disposable cartridges.

Therefore, there is a need for a method for extracting circulating nucleic acids compatible with plastic disposable cartridges.

The present invention aims to remedy all or part of the disadvantages mentioned above.

The present invention fulfills these objectives by providing a method for extracting circulating nucleic acids from a biological fluid, the method comprising the successive steps of:
 a. Providing the biological fluid supposed to contain the circulating nucleic acids;
 b. Contacting the biological fluid with:
  i. a lysis solution comprising at least a chaotropic agent;
  ii. a binding solution comprising at least a PEG derivative designed for cooperating with at least part of the circulating nucleic acids;
  iii. a solid support capable of capturing at least part of the circulating nucleic acids;
 c. Separating said solid support from the lysis solution, from the binding solution and from the biological fluid.

Alternatively, the invention relates to a method for extracting circulating nucleic acids from a biological fluid, the method comprising the successive steps of:
 a. Providing the biological fluid supposed to contain the circulating nucleic acids;
 b. Contacting the biological fluid with:
  i. a lysis solution comprising at least a chaotropic agent;
  ii. a solid support capable of capturing at least part of the circulating nucleic acids;
  iii. a binding solution comprising at least a PEG derivative designed for cooperating with at least part of the circulating nucleic acids;
 c. Separating said solid support from the lysis solution, from the binding solution and from the biological fluid.

Thus, the order of contacting the biological fluid with the lysis solution, the binding solution, and the solid support may be reversed in step b) of the methods as taught herein.

Preferably, the invention relates to a method for extracting circulating nucleic acids from a biological fluid, the method comprising the successive steps of:
 a. Providing the biological fluid supposed to contain the circulating nucleic acids;
 b. Contacting the biological fluid with:
  i. a lysis solution comprising at least a chaotropic agent;
  ii. a binding solution comprising at least a PEG derivative designed for cooperating with at least part of the circulating nucleic acids, wherein the
  iii. a solid support capable of capturing at least part of the circulating nucleic acids;
 c. Separating said solid support from the lysis solution, from the binding solution and from the biological fluid.

Alternatively, the invention relates to a method for extracting circulating nucleic acids from a biological fluid, the method comprising the successive steps of:
 a. Providing the biological fluid supposed to contain the circulating nucleic acids;
 b. Contacting the biological fluid with:
  i. a lysis solution comprising at least a chaotropic agent;
  ii. a solid support capable of capturing at least part of the circulating nucleic acids;
  iii. a binding solution comprising at least a PEG derivative designed for cooperating with at least part of the circulating nucleic acids, wherein the binding solution is free of ethanol and isopropanol;
 c. Separating said solid support from the lysis solution, from the binding solution and from the biological fluid.

Preferably, the invention relates to a method for extracting circulating nucleic acids from a biological fluid, the method comprising the successive steps of:
 a. Providing the biological fluid supposed to contain the circulating nucleic acids;
 b. Contacting the biological fluid with:
  i. a lysis solution comprising at least a chaotropic agent;
  ii. a binding solution comprising at least a PEG derivative designed for cooperating with at least part of the circulating nucleic acids;
  iii. a solid support capable of capturing at least part of the circulating nucleic acids, wherein the solid support comprises a plurality of particles;
 c. Separating said particles from the lysis solution, from the binding solution and from the biological fluid by filtration using at least a filter which is capable of particle retention and which does not bind nucleic acids.

Alternatively, the invention relates to a method for extracting circulating nucleic acids from a biological fluid, the method comprising the successive steps of:
a. Providing the biological fluid supposed to contain the circulating nucleic acids;
b. Contacting the biological fluid with:
 i. a lysis solution comprising at least a chaotropic agent;
 ii. a solid support capable of capturing at least part of the circulating nucleic acids;
 iii. a binding solution comprising at least a PEG derivative designed for cooperating with at least part of the circulating nucleic acids;
c. Separating said solid support from the lysis solution, from the binding solution and from the biological fluid by filtration using at least a filter which is capable of particle retention and which does not bind nucleic acids.

Thus, the present invention solves the problem by providing a binding solution contacting a biological fluid supposed to contain ciNAs, said binding solution comprising at least a PEG derivative. The PEG derivative is designed for cooperating with at least part of said ciNAs so that the capture of at least part of the ciNAs is promoted. To that end, the PEG derivative induces dehydrating effects resulting in precipitation of at least part of the ciNAs, thereby promoting the interactions such as hydrophobic interactions between a solid support contacting the biological fluid and the ciNAs. Hence, contrary to the ciNAs extraction methods according to the prior art, the binding solution according to the present invention is free of ethanol and isopropanol known to induce delaminations. Hence, the method according to the present invention is compatible with disposable cartridges comprising components which are sensitive to ethanol and/or isopropanol based solvents.

Moreover, ethanol and/or isopropanol are reported to inhibit certain downstream applications based on extracted circulating nucleic acids. When it comes to monitoring the evolution of a disease, an even partial inhibition of a PCR assay may introduce bias in the quantification of the monitored circulating tumor nucleic acids thereby providing inaccurate information. Therefore, ethanol and isopropanol have to be carefully evaporated before performing downstream applications, but such evaporation step is difficult to realise when the extraction of ciNAs is performed in a closed container, such as disposable cartridge. Advantageously, the binding solution according to the present invention is ethanol and isopropanol free so that the inhibition of downstream application such as PCR amplification related to the presence of ethanol and/or isopropanol is prevented.

According to an embodiment, the circulating nucleic acids comprise short-chain circulating nucleic acids and long-chain circulating nucleic acids. ciNA are for instance ciDNA or ciRNA, ciDNA being particularly suitable for the method according to the present invention. In the present invention, short-chain circulating nucleic acids are ciNA below about one thousand base pairs, preferentially below about three hundreds base pairs, more preferentially between about one thousand base pairs and about eighteen base pairs, more preferentially between about three hundreds base pairs and about eighteen base pairs.

In an embodiment, the solid support is capable of capturing at least part of the short-chain circulating nucleic acids. It is known from the prior art that short-chain ciNAs are less prone to be captured on the solid support than long-chain ciNAs because short-chain ciNAs offer a limited binding area to the solid support. Thus, in this embodiment, the solid support is designed for promoting the capture of the short-chain circulating nucleic acid.

In the method according to the present invention, the lysis buffer comprising the chaotropic agent is designed for removing at least part of circulating biomolecules susceptible of being coupled to the circulating nucleic acids possibly present in the biological fluid. ciNAs are susceptible of being coupled to circulating biomolecule such as proteins and/or vesicles thereby disturbing the capture of said ciNAs by the solid support. Thus, the lysis buffer promotes the capture of ciNAs by the solid support.

In an embodiment, the method further comprises a filtration step, between step a) and step b), to discard at least part of the debris present in the biological fluid. Debris are known to disturb the capture of ciNAs to the solid support. Thus, the filtration step allows preventing the debris to hinder the extraction of the ciNAs possibly present in the biological fluid.

In one embodiment, the method further comprises a releasing step after step c), in order to release at least part of the circulating nucleic acids captured by said solid support so as to recover at least part of the circulating nucleic acids comprised in said biological fluid.

In an embodiment, said at least part of the circulating nucleic acids captured by said solid support is released from said solid support by using a heater in combination with fluid motion.

According to an embodiment, the method further comprises a nucleic acids amplification step, after step c), to amplify the circulating nucleic acids present in the biological fluid.

In an embodiment, the solid support is capable of capturing at least part of the circulating nucleic acids present in the biological fluid by electrostatic interactions between said solid support and said circulating nucleic acids. Thus, the capture or the release of the ciNAs depends on the electrostatic charge of the solid support.

According to an embodiment, the solid support comprises at least a membrane. In an embodiment, the solid support comprises at least a membrane capable of capturing at least part of the circulating nucleic acids. In an embodiment, the solid support comprises at least a silica membrane. In an embodiment, the solid support comprises at least a silica membrane capable of capturing at least part of the circulating nucleic acids. If the solid support is a silica membrane, then the order of the contacting step b) in the methods of the invention will preferably be:
b. Contacting the biological fluid with:
 i. a lysis solution comprising at least a chaotropic agent;
 ii. a solid support capable of capturing at least part of the circulating nucleic acids;
 iii. a binding solution comprising at least a PEG derivative designed for cooperating with at least part of the circulating nucleic acids;

In an alternative embodiment, the solid support comprises a plurality of particles. In an embodiment, the solid support comprises a plurality of silica particles. In an embodiment, the solid support comprises a plurality of magnetic particles. If the solid support is a plurality of particles, then the order of the contacting step b) in the methods of the invention will preferably be:

b. Contacting the biological fluid with:
  i. a lysis solution comprising at least a chaotropic agent;
  ii. a binding solution comprising at least a PEG derivative designed for cooperating with at least part of the circulating nucleic acids;
  iii. a solid support capable of capturing at least part of the circulating nucleic acids;

According to an embodiment, in step c), at least part of said particles are separated from the binding solution and from the biological fluid by using at least a filter with porosity inferior to the shortest dimension of the particle.

In an embodiment, in step c), at least part of said particles are separated from the bonding solution and from the biological fluid by magnetic actuation.

According to an embodiment, the method is an automated method performed in a cartridge, said cartridge being designed for being operated by an instrument.

In an embodiment, the PEG derivative has a molecular weight between about 6000 Da and about 10000 Da.

According to an embodiment, the circulating nucleic acids comprises circulating DNA.

In one embodiment, the biological fluids is chosen amongst blood, serum, plasma, urine, sputum or a mixture of thereof.

In one embodiment, the method for extracting circulating nucleic acids from a biological fluid comprises the successive steps of:
a. Providing the biological fluid supposed to contain the circulating nucleic acids;
b. Contacting the biological fluid successively with:
  i. a lysis solution comprising at least a chaotropic agent;
  ii. a solid support capable of capturing at least part of the circulating nucleic acids;
  iii. a binding solution comprising at least a PEG derivative designed for cooperating with at least part of the circulating nucleic acids;
c. Separating said solid support from the lysis solution, from the binding solution and from the biological fluid.

Statements (features) and embodiments of the methods or cartridges, as disclosed herein are set herebelow. Each of the statements and embodiments of the invention so defined may be combined with any other statement and/or embodiment unless clearly indicated to the contrary. In particular, any feature or features or statements indicated as being preferred or advantageous may be combined with any other feature or features or statement indicated as being preferred or advantageous. Hereto, the present invention is in particular captured by any one or any combination of one or more of the below numbered aspects and embodiments 1 to 55, with any other statement and/or embodiments.

Numbered statements as disclosed in the present application are:

1. A method for extracting circulating nucleic acids from a biological fluid, the method comprising the successive steps of:
  a. Providing the biological fluid supposed to contain the circulating nucleic acids;
  b. Contacting the biological fluid with:
    i. a lysis solution comprising at least a chaotropic agent;
    ii. a binding solution comprising at least a PEG derivative designed for cooperating with at least part of the circulating nucleic acids;
    iii. a solid support capable of capturing at least part of the circulating nucleic acids;
  c. Separating said solid support from the lysis solution, from the binding solution and from the biological fluid.

2. A method according to statement 1, wherein the circulating nucleic acids comprise short-chain circulating nucleic acids and long-chain circulating nucleic acids.

3. A method according to statement 2, wherein the solid support is capable of capturing at least part of the short-chain circulating nucleic acids.

4. A method according to any one of statements 1 to 3 further comprising a filtration step, between step a) and step b), to discard at least part of the debris present in the biological fluid.

5. A method according to any one of statements 1 to 4 further comprising a releasing step after step c), in order to release at least part of the circulating nucleic acids captured by said solid support so as to recover at least part of the circulating nucleic acids comprised in said biological fluid.

6. A method according to statement 5, wherein said at least part of the circulating nucleic acids captured by said solid support is released from said solid support by using a heater in combination with fluid motion.

7. A method according to any one of statements 1 to 6 further comprising a nucleic acids amplification step, after step c), to amplify the circulating nucleic acids present in the biological fluid.

8. A method according to any one of statements 1 to 7, wherein the solid support is capable of capturing at least part of the circulating nucleic acids present in the biological fluid by electrostatic interactions between said solid support and said circulating nucleic acids.

9. A method according to any one of statements 1 to 8, wherein the solid support comprises at least a membrane.

10. A method according to any one of statements 1 to 9, wherein the solid support comprises a plurality of magnetic particles.

11. A method according to statement 10, wherein in step c), at least part of said particles are separated from the binding solution and from the biological fluid by using at least a filter (38) with porosity inferior to the shortest dimension of the particle.

12. A method according to statements 10 or 11, wherein in step c), at least part of said particles are separated from the binding solution and from the biological fluid by magnetic actuation.

13. A method according to any one of statements 1 to 12, wherein said method is an automated method performed in a cartridge (1), said cartridge (1) being designed for being operated by an instrument.

14. A method according to any one of statements 1 to 13, wherein the PEG derivative has a molecular weight between about 6000 Da and about 10000 Da.

15. A method according to any one of statements 1 to 14, wherein the circulating nucleic acids comprises circulating DNA.

16. A method for extracting circulating nucleic acids from a biological fluid, the method comprising the successive steps of:
  a. Providing the biological fluid supposed to contain the circulating nucleic acids;
  b. Contacting the biological fluid with:
    i. a lysis solution comprising at least a chaotropic agent;
    ii. a binding solution comprising at least a PEG derivative designed for cooperating with at least part of the circulating nucleic acids;
    iii. a solid support capable of capturing at least part of the circulating nucleic acids, wherein the solid support comprises a plurality of particles;

c. Separating said particles from the lysis solution, from the binding solution and from the biological fluid by filtration using at least a filter which is capable of particle retention and which does not bind nucleic acids.
17. The method according to statement 16, wherein the filter is a polyethersulfone (PES) filter.
18. The method according to statement 16 or 17, wherein the circulating nucleic acids comprise short-chain circulating nucleic acids and long-chain circulating nucleic acids.
19. The method according to statement 18, wherein the solid support is capable of capturing at least part of the short-chain circulating nucleic acids.
20. The method according to any one of statements 16 to 19 further comprising a filtration step, between step a) and step b), to discard at least part of the debris present in the biological fluid.
21. The method according to any one of statements 16 to 20 further comprising a releasing step after step c), in order to release at least part of the circulating nucleic acids captured by said solid support so as to recover at least part of the circulating nucleic acids comprised in said biological fluid.
22. The method according to any one of statement 21, wherein said at least part of the circulating nucleic acids captured by said solid support is released from said solid support by using a heater in combination with fluid motion.
23. The method according to any one of statements 16 to 22 further comprising a nucleic acids amplification step, after step c), to amplify the circulating nucleic acids present in the biological fluid.
24. The method according to any one of statements 16 to 23, wherein the solid support is capable of capturing at least part of the circulating nucleic acids present in the biological fluid by electrostatic interactions between said solid support and said circulating nucleic acids.
25. The method according to any one of statements 16 to 24, wherein the particles are selected from the group consisting of silanized particles, oxide particles, and magnetic particles.
26. The method according to any one of statements 16 to 25, wherein the solid support comprises a plurality of magnetic particles.
27. A method according to statement 26, wherein in step c), at least part of said particles are separated from the binding solution and from the biological fluid by using at least a filter (38) with porosity inferior to the shortest dimension of the particle.
28. The method according to statements 26 or 27, wherein in step c), at least part of said particles are separated from the binding solution and from the biological fluid by magnetic actuation.
29. The method according to any one of statements 16 to 28, wherein said method is an automated method performed in a cartridge (1), said cartridge (1) being designed for being operated by an instrument.
30. The method according to any one of statements 16 to 29, wherein the PEG derivative has a molecular weight between about 6000 Da and about 10000 Da.
31. The method according to any one of statements 16 to 30, wherein the circulating nucleic acids comprises circulating DNA.
32. The method according to any one of statements 16 to 31, wherein the method is compatible with disposable cartridges comprising components which are sensitive to ethanol and/or isopropanol based solvents.
33. The method according to any one of statements 16 to 32, wherein the binding solution is free of ethanol and isopropanol.
34. The method according to any one of statements 16 to 33, wherein the method further comprises a washing step with a washing solution in order to wash said solid support, wherein the washing solution is free of an alcohol, preferably wherein the washing solution is free of ethanol and isopropanol.
35. A method for extracting circulating nucleic acids from a biological fluid, the method comprising the successive steps of:
a. Providing the biological fluid supposed to contain the circulating nucleic acids;
b. Contacting the biological fluid with:
a lysis solution comprising at least a chaotropic agent;
a binding solution comprising at least a PEG derivative designed for cooperating with at least part of the circulating nucleic acids, wherein the binding solution is free of ethanol and isopropanol;
a solid support capable of capturing at least part of the circulating nucleic acids;
c. Separating said solid support from the lysis solution, from the binding solution and from the biological fluid.
36. The method according to statement 35, wherein the circulating nucleic acids comprise short-chain circulating nucleic acids and long-chain circulating nucleic acids.
37. The method according to statement 36, wherein the solid support is capable of capturing at least part of the short-chain circulating nucleic acids.
38. The method according to any one of statements 35 to 37 further comprising a filtration step, between step a) and step b), to discard at least part of the debris present in the biological fluid.
39. The method according to any one of statements 35 to 38 further comprising a releasing step after step c), in order to release at least part of the circulating nucleic acids captured by said solid support so as to recover at least part of the circulating nucleic acids comprised in said biological fluid.
40. The method according to any one of statement 39, wherein said at least part of the circulating nucleic acids captured by said solid support is released from said solid support by using a heater in combination with fluid motion.
41. The method according to any one of statements 35 to 40 further comprising a nucleic acids amplification step, after step c), to amplify the circulating nucleic acids present in the biological fluid.
42. The method according to any one of statements 35 to 41, wherein the solid support is capable of capturing at least part of the circulating nucleic acids present in the biological fluid by electrostatic interactions between said solid support and said circulating nucleic acids.
43. The method according to any one of statements 35 to 42, wherein the solid support comprises at least a membrane, preferably a silica membrane.
44. The method according to any one of statements 35 to 43, wherein the solid support comprises a plurality of particles.
45. The method according to any one of statements 35 to 44, wherein the particles are selected from the group consisting of silanized particles, oxide particles, and magnetic particles
46. The method according to any one of statements 35 to 45, wherein the solid support comprises a plurality of magnetic particles.

47. The method according to statement 46, wherein in step c), at least part of said particles are separated from the binding solution and from the biological fluid by using at least a filter (38) with porosity inferior to the shortest dimension of the particle.
48. The method according to statements 46 or 47, wherein in step c), at least part of said particles are separated from the binding solution and from the biological fluid by magnetic actuation.
49. The method according to any one of statements 44 to 48, wherein the step c) of separating said solid support from the lysis solution, from the binding solution and from the biological fluid is performed by filtration using at least a filter which is capable of particle retention and which does not bind nucleic acids.
50. The method according to statement 49, wherein the filter is a polyethersulfone (PES) filter, borosilicate glass microfiber filter, cellulose filter, or asymmetric polysulfone filter, preferably wherein the filter is a PES filter.
51. The method according to any one of statements 35 to 50, wherein said method is an automated method performed in a cartridge (1), said cartridge (1) being designed for being operated by an instrument.
52. The method according to any one of statements 35 to 51, wherein the PEG derivative has a molecular weight between about 6000 Da and about 10000 Da.
53. The method according to any one of statements 35 to 52, wherein the circulating nucleic acids comprises circulating DNA.
54. The method according to any one of statements 35 to 53, wherein the method further comprises a washing step with a washing solution in order to wash said solid support, wherein the washing solution is free of an alcohol, preferably wherein the washing solution is free of ethanol and isopropanol.
55. The method according to any one of statements 35 to 54, wherein the method is compatible with disposable cartridges comprising components which are sensitive to ethanol and/or isopropanol based solvents.

The terms "circulating nucleic acids" or "cell-free nucleic acids", as used herein interchangeably, refer to nucleic acids, such as segments of DNA and/or segments of RNA, found in a biological fluid. Typically, it refers to nucleic acids released from cells in the bloodstream or in biological fluid not containing or no longer containing cells, such as plasma or serum.

In an embodiment, the biological fluid may be plasma, serum, or urine. Preferably, the biological fluid is plasma or serum.

The term "serum" refers to the component of blood that is neither a blood cell nor a clotting factor; the term refers to the blood plasma with the fibrinogens removed.

The term "plasma" defines the colourless watery fluid of the blood that contains no cells, but in which the blood cells (erythrocytes, leukocytes, thrombocytes, etc.) are suspended, containing nutrients, sugars, proteins, minerals, enzymes, etc.

The term "silica" refers to $SiO_2$ crystals and any other form of silica, in particular amorphous silicon oxide and glass powder, alkylsilica, aluminum silicate (zeolite), or, activated silica with—$NH_2$.

Preferably, the invention relates to a method for extracting circulating nucleic acids from a biological fluid, the method comprising the steps of: a) providing the biological fluid supposed to contain the circulating nucleic acids; b) contacting the biological fluid with: a lysis solution comprising at least a chaotropic agent; a binding solution comprising at least a PEG derivative designed for cooperating with at least part of the circulating nucleic acids, wherein the binding solution is free of ethanol and isopropanol; a solid support capable of capturing at least part of the circulating nucleic acids; and c) separating said solid support from the lysis solution, from the binding solution and from the biological fluid.

In an embodiment, the step b) may be performed by contacting the biological fluid with the lysis solution; the binding solution; and the solid support, in any order.

In an embodiment, the binding solution may further comprise at least a surfactant. The surfactant may be for example polysorbaat 20 (Tween® 20, PEG(20)sorbitaan monolauraat, or Polyoxyethyleensorbitaan monolauraat).

In an embodiment, the circulating nucleic acids may comprise short-chain circulating nucleic acids and long-chain circulating nucleic acids.

In an embodiment, the solid support may be capable of capturing at least part of the short-chain circulating nucleic acids.

In an embodiment, the method may further comprise a filtration step, between step a) and step b), to discard at least part of the debris present in the biological fluid.

In an embodiment, the method may further comprise a releasing step after step c), in order to release at least part of the circulating nucleic acids captured by said solid support so as to recover at least part of the circulating nucleic acids comprised in said biological fluid.

In an embodiment, at least part of the circulating nucleic acids captured by said solid support may be released from said solid support by using a heater in combination with fluid motion.

In an embodiment, the method may further comprise a nucleic acids amplification step, after step c), to amplify the circulating nucleic acids present in the biological fluid.

In an embodiment, the solid support may be capable of capturing at least part of the circulating nucleic acids present in the biological fluid by electrostatic interactions between said solid support and said circulating nucleic acids.

In an embodiment, the solid support may comprise at least a membrane. In an embodiment, the solid support may comprise at least a membrane capable of capturing at least part of the circulating nucleic acids. In an embodiment, the solid support may comprise at least a silica membrane. In an embodiment, the solid support may comprise at least a silica membrane capable of capturing at least part of the circulating nucleic acids. In these embodiments, in step b), the biological fluid may be first contacted with the lysis solution and the solid support in order to capture at least part of the circulating nucleic acids on the solid support, and thereafter the biological fluid may be contacted with the binding solution in order to remove at least part of the proteins.

In an alternative embodiment, the solid support may comprise a plurality of particles. In an embodiment, the solid support may comprise a plurality of particles capable of capturing at least part of the circulating nucleic acids. In these embodiments, in step b), the biological fluid may be first contacted with the lysis solution and the binding solution, and thereafter the biological fluid may be contacted with the solid support in order to capture at least part of the circulating nucleic acids on the solid support.

In an embodiment, the particles may be silanized beads, oxide beads, or magnetic beads. In an embodiment, the particles may be selected from the group consisting of silanized particles, oxide particles, and magnetic particles.

The term "particles" as used herein, refers to particles with a size of from 0.5 to 5.0 µm, preferably of from 1.0 to 5.0 µm, preferably of from 2.0 to 4.0 µm. Such particles are known in nucleic acid purification techniques. Exemplary particles may have a particle size of 3 µm. The size of the particles, preferably silanized particles, oxide particles, or magnetic particles, can be determined by laser diffraction, for instance using a Mastersizer (Malvern, Worcestershire, UK). The size of the particle may be regarded as the mean size. The size of the particle may be that across the maximum width.

The terms "particles" and "beads" may be used interchangeable herein.

The term "silanized particles" refers to particles comprising $SiO_2$ or any other form of silica, in particular amorphous silicon oxide or glass powder, alkylsilica, aluminum silicate (zeolite), or activated silica with —$NH_2$.

The terms "silanized particles" and "silica particles" may be used interchangeably herein.

The term "oxide particles" refers to silicium oxide ($SiO_2$) particles or metal oxide particles such as preferably iron oxide particles.

The term "magnetic particles" refers to particles that are susceptible to be attracted by magnetism.

The particles may be coated particles.

In an embodiment, the solid support may comprise a plurality of magnetic particles. In an embodiment, the solid support may comprise a plurality of superparamagnetic particles.

In an embodiment, in step c), at least part of said particles are separated from the binding solution and from the biological fluid by using at least a filter (38) with porosity inferior to the shortest dimension of the particle.

In a further embodiment of the methods as taught herein, in step c), at least part of said particles are separated from the binding solution and from the biological fluid by magnetic actuation.

In an embodiment, the separation of the solid support, in particular the particles, from the lysis solution, from the binding solution, and from the biological fluid may be performed by filtering using a filter capable to retain the particles.

In an embodiment, the separation of the solid support, in particular the particles, from the lysis solution, from the binding solution, and from the biological fluid may be performed by filtering using a filter which does not bind nucleic acids.

In an embodiment, the step c) of separating said solid support from the lysis solution, from the binding solution and from the biological fluid may be performed by filtration using at least a filter which is capable of particle retention and which does not bind nucleic acids.

Such a filter advantageously allows to retain all the particles and does not bind any DNA.

In an embodiment, the filter may be composed of hydrophilic material.

In an embodiment, the filter may be a polyethersulfone (PES) filter, borosilicate glass microfiber filter, cellulose filter, or asymmetric polysulfone filter.

An example of an asymmetric polysulfone filter is Vivid™ Plasma Separation Membranes (Pall Corporation).

In an embodiment, the filter may be substantially composed of or substantially made of polyethersulfone (PES). Preferably, the filter is a PES filter. The PES filter advantageously allows retaining all the particles, while not binding any nucleic acids (e.g., DNA) or proteins. In contrast, many prior art materials, such as Polytetrafluoroethylene (PTFE) filters, would either absorb proteins or nucleic acids. The PES filter advantageously allows easy filtration of milliliter volumes of liquids (such as more than 30 milliliters of liquid). The PES filter advantageously allows passing all the liquids without a significant pressure increase. Such a PES filter is also advantageous in that it is inert for the chemicals and temperatures used in the methods as taught herein.

In an embodiment, the PES filter may have a pore size of 0.45 µm. Such pore size allows ensuring complete capturing of the particles. In an embodiment, the PES filter may be asymmetric whereby one side of the filter has a pore smaller pore size than the other side of the filter. For example, the PES filter may have on one side of the filter a pore size of about 20 µm that decreases to 0.45 µm on the other side of the filter. Such PES filters advantageously allow achieving high volume flow at low transmembrane pressure.

In an embodiment, said method may be an automated method performed in a cartridge (1), said cartridge (1) being designed for being operated by an instrument.

In an embodiment, the PEG derivative may have a molecular weight between about 6000 Da and about 10000 Da.

In an embodiment, the circulating nucleic acids may comprise circulating DNA.

In an embodiment, the binding solution is free of an alcohol. In an embodiment, the binding solution may not comprise an alcohol.

The term "alcohol" as used herein, refers to any organic compound in which the hydroxyl functional group (—OH) is bound to a saturated carbon atom. Preferably, the alcohol is a monohydric alcohol such as methanol ($CH_3OH$); ethanol ($C_2H_5OH$); isopropyl alcohol, 2-propanol, or isopropanol ($C_3H_7OH$); butyl alcohol or butanol ($C_4H_9OH$); pentanol ($C_5H_{11}OH$); or hexadecan-1-ol ($C_{16}H_{33}OH$).

In a preferred embodiment, the alcohol is ethanol and/or isopropanol.

In an embodiment, the method may further comprise a washing step with a washing solution in order to wash said solid support. For example, the solid support may be washed after separating said solid support from the lysis solution, from the binding solution and from the biological fluid. In an embodiment, the method may further comprise, after step c), a washing step with a washing solution in order to wash said solid support.

In an embodiment, the one or more washing solutions may be free of an alcohol. In an embodiment, the one or more washing solutions may not comprise an alcohol. Preferably, the one or more washing solutions are free of ethanol and isopropanol.

In an embodiment, the binding solution and one or more washing solutions may be free of an alcohol. In an embodiment, the binding solution and one or more washing solutions may not comprise an alcohol. Preferably, the binding solution and one or more washing solutions are free of ethanol and isopropanol.

In an embodiment, the binding solution, the lysis solution, the one or more washing solutions, and the elution solution may be free of an alcohol. In an embodiment, the binding solution, the lysis solution, the one or more washing solutions, and the elution solution may not comprise an alcohol. Preferably, the binding solution, the lysis solution, the one or more washing solutions, and the elution solution are free of ethanol and isopropanol.

In an embodiment, the method may be compatible with disposable cartridges comprising components that are sensitive to ethanol and/or isopropanol based solvents.

The present invention is further illustrated by the following detailed description set forth in view of the appended drawing, which represent an exemplary and explanatory embodiment of a method for extracting circulating nucleic acids from a biological fluid, wherein:

FIG. 1 is a schematic view of a cartridge designed to perform the method according to an embodiment of the present invention.

In the present embodiment, the method for extracting ciNAs from a biological fluid according to the present invention is performed with a disposable cartridge 1, shown on FIG. 1, designed for being operated by an instrument (not shown). The cartridge 1 is formed of a container 2 that comprises two rectangular major faces, a first major face 3 and a second major face 4, that delimitate the width of the container 2, as shown on FIG. 1. The first major face 3 is designed for being placed opposite the instrument. The second major face 4 comprises an extraction area 5 designed for being functionalized by an operator.

The cartridge 1 comprises six circuits 6, said circuits 6 being in fluid connection with one collecting chamber 7 located between the first major face 3 and the second major face 4. Each circuit 6 comprises:

- a port 8 in fluid connection with the extraction surface 5 on one side and to a channel 9 on the opposite side;
- the channel 9 further comprising a valve 10.

Each port 8 is designed for receiving one tube 11. To that end, each tube 11 comprises a tip 12 located at one end of said tube and designed for being inserted into one port 8 when said tube 11 is positioned perpendicularly to the extraction area 5 of the cartridge 1. The tip 12 further comprises a through hole 13 leading to the internal volume of said tube 11. Concerning the valves 10, each valve 10 is operated by the instrument to control the fluid connection between one port 8 and the collecting chamber 7.

In this respect, the six circuits 6 functionalizing the cartridge 1 are:

- a sample circuit comprises a sample port 14 designed for receiving a sample tube 15, said sample port 14 being in fluid connection with a sample channel 16 comprising a sample valve 17;
- a first washing circuit comprises a first washing port 18 designed for receiving a first washing tube 19, said first washing port 18 being in fluid connection with a first washing channel 20 comprising a first washing valve 21;
- a second washing circuit comprises a second washing port 22 designed for receiving a second washing tube 23, said second washing port 22 being in fluid connection with a second washing channel 24 comprising a second washing valve 25;
- an elution circuit comprises a elution port 26 designed for receiving a elution tube 27, said elution port 26 being in fluid connection with a elution channel 28 comprising an elution valve 29;
- a nucleic acid circuit comprises a nucleic acid port 30 designed for receiving a nucleic acid tube 31, said nucleic acid port 30 being in fluid connection with a nucleic acid channel 32 comprising an nucleic acid valve 33;
- a waste circuit comprises a waste port 34 designed for receiving a waste tube 35, said waste port 34 being in fluid connection with a waste channel 36 comprising a waste valve 37.

The method according to the present invention is initiated by providing the biological fluid comprising the ciNAs. The biological fluid is constituted of 5 ml of plasma that comprised a concentration of ciDNAs to be determined, said ciDNAs further comprising short-chain ciDNAs and long-chain ciDNAs.

In the present case, the collecting chamber 7 is equipped with a polyethersulfone (PES) filter 38 designed for collecting a solid support capable of capturing at least part of the ciDNAs. In the present case, the solid support comprises a plurality of magnetic particles (not shown). To that end, the filter 38 has porosity inferior to the shortest dimension of the magnetic particles. Additionally, the collecting chamber 7 is contacting a heater (not shown) comprised in the instrument, to heat the collecting chamber 7.

In the present embodiment, the magnetic particles are magnetic silica beads designed for capturing and then releasing at least part of the ciDNAs via electrostatic interactions. The magnetic silica beads are positively charged in an acidic media thereby allowing the capture at least part of the negatively charged ciDNAs. In a basic media, said magnetic silica beads turn out to be negatively charged thereby fostering the release of the captured ciDNAs. Advantageously, such magnetic silica beads can also be collected by magnetic actuation via a magnet placed in the vicinity of the collecting chamber 7. In another embodiment not shown here, the solid support comprises a membrane, preferably a silica membrane.

Before starting the extraction of the ciDNAs comprised in the plasma, two solutions required for the extraction method according to the present invention are prepared by the operator, a first solution and a second solution. The first solution is a binding solution comprising 4 mL of PEG 8000 (CAS Number 25322-68-3), 100 µl of Tween® 20 (CAS Number 9005-64-5) and lysis buffer (quantum sufficient for 40 ml). The second solution is a washing solution comprising Sodium Citrate 20 nM diluted six times in water (molecular biology grade) at pH 3. Then, the cartridge 1 is loaded on the instrument and the sample tube 15, the first washing tube 19, the second washing tube 23, the elution tube 27, the nucleic acid tube 31 and waste tube 35 are inserted into their corresponding ports 8. Thus in the present embodiment, when the valves 10 are in opened position, each tube 11 is in fluid connection with the collecting chamber 7. Additionally, 1 ml of a lysis solution is loaded in the first washing tube 19, 1 ml of the washing solution is loaded in the second washing tube 23, 1100 µl of Tris buffer is loaded in the elution solution tube 27. The lysis solution comprises at least a chaotropic agent comprising guanidinium salts in the present case.

In a first step of this embodiment, the plasma is filtered through an additional filter (not shown) to discard at least part of the debris present in the plasma before loading the filtered plasma into the sample tube 15.

Then in a second step, the filtered plasma contained in the sample tube 15 is incubated for 10 minutes at room temperature with respectively 10 ml of lysis solution and 200 µl of silica beads solution. In the present embodiment, the lysis solution aims at removing at least part of the proteins and the vesicles coupled to the ciDNAs present in the plasma. This second step is an initial capture step that allows the solid support to capture of at least part of the long-chain ciDNAs present in the plasma.

Then 9 ml of the binding solution prepared as mentioned previously is loaded in the sample tube 15 to constitute a reaction mixture, said reaction mixture being incubated in the sample tube 15 for 5 minutes still at room temperature. Subsequently, the instrument opens the sample valve 17 of the sample channel 16 in fluid connection with the sample tube 15 thus allowing the transfer of the reaction mixture into the collecting chamber 7. Then, the reaction mixture is filtered through the polyethersulfone (PES) filter 38 capable of collecting at least part of the magnetic silica beads, the flow through being transferred to the waste tube 35 via the waste valve 37 opened by the instrument.

In the next step, the instrument operates successively the first washing valve 21 and the second washing valve 25 to wash the magnetic silica beads collected on the filter 38. Thus, firstly, the lysis solution contained in the first washing tube 19 and secondly the washing solution contained in the second washing tube 23 contact the magnetic silica beads collected on the filter 38, the flow through being transferred to the waste tube 35 via the waste valve 37 opened by the instrument.

The release of the ciDNAs captured on the magnetic silica beads is operated in a two-step process. First, the instrument operates the elution valve 29 to contact the magnetic silica beads collected on the filter 38 with 1000 μl of the Tris buffer contained in the elution tube 27 to neutralize the positively charged magnetic silica beads, the flow through being again transferred to the waste tube 35 via the waste valve 37 opened by the instrument. Secondly, the instrument switches on the heater at 70° C. to heat the collecting chamber 7 containing the magnetic silica beads and then opens the nucleic acid valve 31 and the elution valve 29 to pump 100 μl Tris buffer back and forth from the elution tube 27 to the nucleic acid tube 31 via the filter 38 containing the magnetic silica beads for 10 minutes. Thus, at least part of the ciDNAs captured by the magnetic silica beads is released therefrom by using the heater in combination with fluid motion of the Tris buffer. After 10 min, the resulting elution buffer is definitively transferred in the nucleic acid tube 31 to store the Tris solution comprising the ciDNAs extracted from the plasma.

Advantageously, a nucleic acid amplification step such as a PCR amplification is performed on the solution comprised in the nucleic acid tube to amplify the ciDNAs present in the plasma.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

The invention claimed is:

1. A method for extracting short-chain circulating nucleic acids having a length less than three hundred base pairs from serum or plasma, the method comprising the successive steps of:
   (a) preparing a reaction mixture that is free of ethanol and isopropanol by combining the following components with the serum or plasma;
      (i) a lysis solution comprising at least a chaotropic agent;
      (ii) a binding solution comprising at least a PEG derivative; and
      (iii) a solid support capable of capturing at least part of the short-chain circulating nucleic acids in the reaction mixture; and
   (b) separating the solid support from the reaction mixture, thereby extracting the short-chain circulating nucleic acids from the serum or plasma.

2. The method according to claim 1 further comprising filtering the serum or plasma to remove any insoluble debris present in the serum or plasma prior to preparing the reaction mixture of step (a).

3. The method according to claim 1 further comprising a step (c) after step (b), wherein step (c) comprises releasing at least part of the short-chain circulating nucleic acids captured by the solid support so as to recover at least part of the short-chain circulating nucleic acids from the serum or plasma.

4. The method according to claim 3, wherein the at least part of the short-chain circulating nucleic acids captured by the solid support is released from the solid support by applying heat in combination with fluid motion.

5. The method according to claim 3 further comprising a further step (d) after step (c), wherein step (d) comprises amplifying the released short-chain nucleic acids.

6. The method according to claim 1, wherein the solid support is capable of capturing at least part of the short-chain circulating nucleic acids present in the serum or plasma by electrostatic interactions between the solid support and the short-chain circulating nucleic acids.

7. The method according to claim 1, wherein the solid support comprises at least a silica membrane.

8. The method according to claim 1, wherein the solid support comprises a plurality of particles.

9. The method according to claim 8, wherein the particles are selected from the group consisting of silanized particles, oxide particles, and magnetic particles.

10. The method according to claim 1, wherein the solid support comprises a plurality of magnetic particles.

11. The method according to claim 10, wherein in step (b) at least part of the particles are separated from the reaction mixture by using at least a filter with porosity that is less than the shortest dimension of the particle.

12. The method according to claim 10, wherein in step (b) at least part of the particles are separated from the reaction mixture by magnetic actuation.

13. The method according claim 8, wherein the step (b) of separating the solid support comprising a plurality of particles from the reaction mixture is performed by filtering the plurality of particles using at least a filter which is capable of retaining the plurality of particles and which does not bind nucleic acids.

14. The method according to claim 13, wherein the filter is a selected from the group consisting of a polyethersulfone (PES) filter, a borosilicate glass microfiber filter, a cellulose filter, and an asymmetric polysulfone filter.

15. The method according to claim 1, wherein the method is an automated method performed in a cartridge, the cartridge being designed for being operated by an instrument.

16. The method according to claim 1, wherein the PEG derivative has a molecular weight between about 6000 Da and about 10000 Da.

17. The method according to claim 1, wherein the circulating short-chain nucleic acids comprise circulating DNA.

18. The method according to claim 1, wherein the method further comprises a washing step using a washing solution in order to wash the solid support, wherein the washing solution is free of an alcohol.

19. The method according to claim 1, wherein the method is compatible with disposable cartridges comprising components that are sensitive to ethanol and/or isopropanol based solvents.

20. A method for extracting short-chain circulating nucleic acids having a length less than three hundred base pairs from serum or plasma from a subject having cancer, the method comprising the successive steps of:
   (a) preparing a reaction mixture that is free of ethanol and isopropanol by combining the following components with the serum or plasma;
      (i) a lysis solution comprising at least a chaotropic agent;

(ii) a binding solution comprising at least a PEG derivative; and
(iii) a solid support capable of capturing at least part of the short-chain circulating nucleic acids in the reaction mixture; and
(b) separating the solid support from the reaction mixture, thereby extracting the short-chain circulating nucleic acids from the serum or plasma.

* * * * *